United States Patent
Bischof et al.

(10) Patent No.: US 7,344,530 B2
(45) Date of Patent: Mar. 18, 2008

(54) THERMAL SURGICAL PROCEDURES AND COMPOSITIONS

(75) Inventors: John C. Bischof, St. Paul, MN (US); John D. Belcher, Minneapolis, MN (US); Gregory M. Vercellotti, Stillwater, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 160 days.

(21) Appl. No.: 10/810,956

(22) Filed: Mar. 26, 2004

(65) Prior Publication Data

US 2005/0080405 A1    Apr. 14, 2005

Related U.S. Application Data

(60) Provisional application No. 60/457,691, filed on Mar. 26, 2003.

(51) Int. Cl.
*A61B 18/02* (2006.01)

(52) U.S. Cl. .......................................... 606/21; 128/898

(58) Field of Classification Search ............. 606/20–31; 607/96–105; 128/898
See application file for complete search history.

(56) References Cited

U.S. PATENT DOCUMENTS

| | | | |
|---|---|---|---|
| 4,072,152 A | | 2/1978 | Linehan |
| 4,140,109 A | | 2/1979 | Savic et al. |
| 4,252,130 A | | 2/1981 | Le Pivert |
| 4,275,734 A | | 6/1981 | Mitchiner |
| 4,306,568 A | | 12/1981 | Torre |
| 4,441,486 A | * | 4/1984 | Pounds .......................... 601/3 |
| 4,483,341 A | | 11/1984 | Witteles |
| 4,528,979 A | * | 7/1985 | Marchenko et al. .......... 606/21 |
| 4,872,458 A | * | 10/1989 | Kanehira et al. .............. 606/31 |
| 4,920,978 A | * | 5/1990 | Colvin ........................ 607/102 |
| 4,946,460 A | | 8/1990 | Merry et al. |
| 5,067,952 A | * | 11/1991 | Gudov et al. .................. 606/28 |
| 5,139,496 A | | 8/1992 | Hed |
| 5,385,148 A | * | 1/1995 | Lesh et al. ................... 600/471 |
| 5,403,311 A | * | 4/1995 | Abele et al. ................... 606/49 |
| 5,425,940 A | * | 6/1995 | Zimmerman et al. ...... 424/85.1 |
| 5,472,441 A | * | 12/1995 | Edwards et al. .............. 606/41 |

(Continued)

FOREIGN PATENT DOCUMENTS

WO    97/35601 A    10/1997

(Continued)

OTHER PUBLICATIONS

Falk MH, Issels RD. Hyperthermia in oncology. International Journal of Hyperthermia 2001; 17(1):1-18.*

(Continued)

*Primary Examiner*—Roy D Gibson
(74) *Attorney, Agent, or Firm*—Mueting Raasch & Gebhardt, P.A.

(57) ABSTRACT

Methods, compositions, and systems useful to enhance a thermal surgical procedure are described. Compositions include at least one compound effective to induce an inflammatory response in biological material identified to undergo a thermal surgical procedure. Methods and systems include providing compositions of the invention to biological materials and treating biological materials with an inflammation inducing composition for a time, amount, and type effective to induce inflammation in at least a portion of the biological material.

18 Claims, 3 Drawing Sheets

U.S. PATENT DOCUMENTS

| | | | |
|---|---|---|---|
| 5,536,267 A | | 7/1996 | Edwards et al. |
| 5,620,479 A | * | 4/1997 | Diederich ........................ 601/3 |
| 5,654,279 A | | 8/1997 | Rubinsky et al. |
| 5,714,170 A | * | 2/1998 | Baserga et al. .............. 424/573 |
| 5,720,743 A | | 2/1998 | Bischof et al. |
| 5,722,985 A | * | 3/1998 | Pettus ......................... 606/180 |
| 5,741,248 A | | 4/1998 | Stern et al. |
| 5,807,395 A | | 9/1998 | Mulier et al. |
| 5,902,582 A | * | 5/1999 | Hung ....................... 424/130.1 |
| 5,906,636 A | | 5/1999 | Casscells, III et al. |
| 6,004,269 A | * | 12/1999 | Crowley et al. ............. 600/439 |
| 6,041,787 A | | 3/2000 | Rubinsky |
| 6,146,897 A | * | 11/2000 | Cohenford et al. ........... 436/63 |
| 6,190,378 B1 | * | 2/2001 | Jarvinen ........................ 606/21 |
| 6,231,536 B1 | * | 5/2001 | Lentz ......................... 604/5.04 |
| 6,235,018 B1 | | 5/2001 | LePivert |
| 6,305,380 B1 | * | 10/2001 | Hellstrand et al. ........... 128/898 |
| 6,306,132 B1 | * | 10/2001 | Moorman et al. ............ 606/41 |
| 6,350,276 B1 | | 2/2002 | Knowlton |
| 6,451,044 B1 | * | 9/2002 | Naghavi et al. .............. 607/96 |
| 6,514,251 B1 | * | 2/2003 | Ni et al. ........................ 606/41 |
| 6,622,731 B2 | | 9/2003 | Daniel et al. |
| 6,648,879 B2 | | 11/2003 | Joye et al. |
| 6,749,624 B2 | * | 6/2004 | Knowlton ................... 607/104 |
| 6,772,766 B2 | * | 8/2004 | Gallo et al. .................. 128/898 |
| 6,805,701 B1 | * | 10/2004 | Cortes ......................... 607/89 |
| 7,083,612 B2 | * | 8/2006 | Littrup et al. ................. 606/21 |
| 2001/0017137 A1 | * | 8/2001 | Burbank et al. ............ 128/898 |
| 2002/0042609 A1 | * | 4/2002 | Kelman et al. .............. 606/21 |
| 2002/0095143 A1 | | 7/2002 | Key |
| 2002/0120238 A1 | * | 8/2002 | McGuckin et al. ......... 604/187 |
| 2002/0133148 A1 | * | 9/2002 | Daniel et al. ................. 606/34 |
| 2003/0050268 A1 | * | 3/2003 | Krieg et al. .................. 514/44 |
| 2003/0120267 A1 | * | 6/2003 | Kaufman et al. ............. 606/14 |
| 2003/0220639 A1 | * | 11/2003 | Chapelon et al. ............ 606/33 |
| 2005/0080405 A1 | * | 4/2005 | Bischof et al. ............... 606/20 |
| 2005/0215991 A1 | * | 9/2005 | Altman et al. ................ 606/41 |

FOREIGN PATENT DOCUMENTS

| | | |
|---|---|---|
| WO | 98/05380 A | 2/1998 |
| WO | WO 03/105672 A2 | 12/2003 |

OTHER PUBLICATIONS

U.S. Appl. No. 10/461,763, filed Jun. 13, 2003, Bischof et al.

Ablin, "An Appreciation and Realization of the Concept of Cryoimmunology," *Percutaneous Prostate Cryoablation*, St. Louis, MO, Quality Medical Publ., Inc.; 1995; title page, p. 136.

Aliev et al., "Morphological features of regeneration of rabbit aortic endothelium after cryoinduced vascular damage," *J. Submicrosc. Cytol. Pathol.*, 1999; 31(4):495-502.

Arnott, "On the Treatment of Cancer, by the Regulated Application of an Anesthetic Temperature," J. Churchill, London, England, 1851; title page, and 1 pg. (entire document cannot be copied due to condition of original book).

Arturson, "Capillary Permeability in Experimental Rapid Freezing with Rapid and Slow Rewarming," *Acta. Chir. Scand.*, 1966; 131:402-407.

Asahina et al., "A Stable State of Frozen Protoplasm with Invisible Intracellular Ice Crystals Obtained by Rapid Cooling," *Exp. Cell Res.*, 1970; 59:349-358.

Barker et al., "The Effect of Superoxide Dismutase on the Skin Microcirculation after Ischemia and Reperfusion," *Prog. Appl. Microcirc.*, 1987; 12:276-281.

Bellman et al., "Vascular Reactions after Experimental Cold Injury," *Angiology*, 1956; 7:339-367.

Bellman et al., "Transformation of the Vascular System in Cold-Injured Tissue of the Rabbit's Ear," *Angiology*, 1960; 11:108-125.

Bischof et al., "An Analytical Study of Cryosurgery in the Lung," *ASME J. Biomech. Eng.*, 1992; 114:467-472.

Bischof et al., "Microscale Heat and Mass Transfer of Vascular and Intracellular Freezing in the Liver," *J. Heat Trans.*, 1993; 115:1029-1035.

Bischof et al., "A Morphological Study of Cooling Rate Response in Normal and Neoplastic Human Liver Tissue: Cryosurgical Implications," *Cryobiology*, 1993; 30:482-492.

Bischof et al., "Rectal Protection During Prostate Cryosurgery: Design and Characterization of an Insulating Probe," *Cryobiology*, 1997; 34(1):80-92.

Bischof et al., "Cryosurgery of Dunning AT-1 Rat Prostate Tumor: Thermal, Biophysical, and Viability Response at the Cellular and Tissue Level," *Cryobiology*, 1997; 34(1):42-69.

Bischof et al., "A parametric study of freezing injury in ELT-3 uterine leiomyoma tumour cells," *Human Reproduction*, 2001; 16:340-348.

Bischof, "Mechanisms of Injury During Freezing: Cryosurgery of Prostate," Presentation, Minnesota's Medical Device Community Forum, Apr. 24-25, 2003, Minneapolis, MN, 20 pgs.

Bischof, John C., "Establishing the Efficacy of Cryomyolysis—Cryosurgery of Uterine Fibroids," Grant Abstract, Grant No. NSF-BES 9703326 [online]. National Science Foundation—BES Division, Sep. 15, 1997 to Aug. 31, 2002 [retrieved on Jul. 1, 2003]. Retrieved from the Internet: <URL:https:www.fastlane.nsf.gov/servlet/showaward?award=9703326>; 2 pgs.

Bischof, John C., "Establishment of Mechanisms of Cryodestruction," Grant Abstract, Grant No. 5R29CA075284-05 [online]. National Cancer Institute, Jul. 15, 1998 to Jun. 30, 2003 [retrieved on Jul. 1, 2003]. Retrieved from the Internet:<URL:http:crisp.cit.nih.gov/crisp/CRISP_LIB.getdoc?textkey=6513112&p_grant_num=5R29CA075284-05&p_query=&ticket=3953348&p_audit_session_id=18077139&p_keywords=>; 2 pgs.

Bonney et al., "Cryosurgery in Prostatic Cancer: Elimination of Local Lesion," *Urology*, 1983; 22:8-15.

Bourne et al., "Analysis of Microvascular Changes in Frostbite Injury," *J. Surg. Res.*, 1986; 40:26-35.

Bowers et al., "Ultrastructural Studies of Muscle Cells and Vascular Endothelium Immediately after Freeze-Thaw Injury," *Cryobiology*, 1973; 10:9-21.

Chao et al., "Pre-treatment inflammation induced by TNF-alpha cryosurgical injury on human prostate cancer," *Cryobiology*, 2004;49(1):10-27.

Chosy et al., "Monitoring Renal Cryosurgery: Predictors of Tissue Necrosis in Swine," *Journal of Urology*, 1998; 159:1370-1374.

Clarke et al., "Timing Dependency in Cryo-Chemo Combination Therapy: Model Cell Systems," *Cryobiology*, Abstracts, 36th Annual Meeting, 1999; 39:320.

Comini et al., "Thermal Aspects of Cryosurgery," *ASME J. Heat Transfer*, 1976; 98:543-549.

Cooper, "Cryogenic Surgery. A New Method of Destruction or Extirpation of Benign or Malignant Tissues," *New Eng. J. Med.*, 1963; 268:743-749.

Cooper et al., "Analytical Prediction of the Temperature Field Emanating from a Cryogenic Surgical Cannula," *Cryobiology*, 1970; 7:79-93.

Cooper et al., "Rate of Lesion Growth Around Spherical and Cylindrical Cryoprobes," *Cryobiology*, 1971; 7:183-190.

Cosman et al., "An Integrated Cryomicroscopy System," *Cryo-Letters*, 1989; 10:17-38.

Crismon et al., "Studies on Gangrene Following Cold Injury. V: The Use of Fluorescein as an Indicator of Local Blood Flow: Fluorescein Tests in Experimental Frostbite," *J. Clin. Invest.*, 1947; 26:268-276.

Cummings et al., "Increased vascular permeability evoked by cold injury," *Pathology*, 1973; 5:107-116.

Dachs et al., "The molecular response of mammalian cells to hypoxia and the potential for exploitation in cancer therapy," *Brit. J. Cancer*, 1996; 74(Suppl. 27):S126-S131.

Daum et al., "Vascular Casts Demonstrate Microcirculatory Insufficiency in Acute Frostbite," *Cryobiology*, 1987; 24:65-73.

Diller et al., "Water Transport Through a Multicellular Tissue During Freezing: A Network Thermodynamic Modeling Analysis," *Cryo-Letters*, 1990; 11:151-162.

Dilley et al., "Laboratory and Animal Model Evaluation of the Cryotech LCS 2000 in Hepatic Cryotherapy," *Cryobiology*, 1993; 30:74-85.

Echlin, *Low-Temperature Microscopy and Analysis*, New York, NY, Plenum Press, 1992, cover page, title page and table of contents only:11 pgs.

Elliot et al., "Ice Pattern Formation in Mammary Tissue from Sprague-Dawley Rats," *Cryobiology*, Abstracts, 35th Annual Meeting, 1998; 37:451.

Folkman, "The Vascularization of Tumors," *Sci. Am.*, 1976; 234:59-64 & 70-73.

Fraser et al., "Observations on Ultra-Frozen Tissue," *Br. J. Surg.*, 1967; 54:770-776.

Fukumura et al., "Tumor Necrosis Factor Alpha-induced Leukocyte Adhesion in Normal and Tumor Vessels: Effect of Tumor Type, Transplantation Site, and Host Strain," *Cancer Research*, 1995; 55(21):4824-4829.

Gage et al., "Effect of Varying Freezing and Thawing Rates in Experimental Cryosurgery," *Cryobiology*, 1985; 22(2):175-182.

Gage, "Cryosurgery in the Treatment of Cancer," *Surg., Gynecol. Obstet.*, 1992; 174(1):73-92.

Gage et al., "Mechanisms of Tissue Injury in Cryosurgery," *Cryobiology*, 1998; 37(3):171-186.

Gilbert et al., "Real Time Ultrasonic Monitoring of Hepatic Cryosurgery," *Cryobiology*, 1985; 22:319-330.

Gilbert et al., "Solid-Liquid Interface Monitoring with Ultrasound During Cryosurgery," *ASME 85-WA/HT-83*, 1985:1-10.

Gill et al., "Renal cryosurgery," *Urology*, 1999, 54:215-219.

Gupta et al., "A Novel Technique for Culture of Human Dermal Microvascular Endothelial Cells Under Either Serum-free or Serum-supplemented Conditions: Isolation by Panning and Stimulation with Vascular Endothelial Growth Factor," *Exp. Cell Res.*, 1997; 230(2):244-251.

Han et al., "Modification and Use of Eutectic Formation to Enhance Direct Cell Injury," Powerpoint Presentation, *39th Annual Meeting of the Society for Cryobiology*, Breckenridge, CO, Jul. 28-31, 2002; 18 pgs.

Han et al., "Modification and use of eutectic formation to enhance direct cell injury," Abstract, 39th Annual Meeting of the Society for Cryobiology, Breckenridge, CO, Jul. 28-31, 2002; *Cryobiology*, 2002; 45:2 pgs.

Han et al., "Thermal property measurements in biological solutions at subzero temperatures," Abstract, 39 th Annual Meeting of the Society for Cryobiology, Breckenridge, CO, Jul. 28-31, 2002; *Cryobiology*, 2002; 45: 3 pgs.

Han et al., "Phase Change Behavior of Biomedically Relevant Solutions," *Proceedings of IMECE2002, ASME International Mechanical Engineering Congress & Exposition, IMECE2002-32549*, New Orleans, LA, Nov. 17-22, 2002; 7 pgs.

Han et al., "Enhancement of cell and tissue destruction in cryosurgery by use of eutectic freezing," Powerpoint Presentation, *2003 SPIE Conference*, San Jose, CA, Jan. 25-31, 2003; 25 pgs.

Han et al., "Enhancement of Direct Cell Injury During Freezing AT-1 Tumor Tissues by Use of Eutectic Crystallization," *2003 Summer Bioengineering Conference*, Key Biscayne, FL, Jun. 25-29, 2003; 2 pgs.

Hayakawa et al., "Comparative Immunological Studies in Rats Following Cryosurgery and Surgical Excision of 3-Methylcholanthrene-Induced Primary Autochthonous Tumors," *Gann*, 1982; 73:462-469.

Hayes et al., "Prediction of Local Cooling Rates and Cell Survival During the Freezing of a Cylindrical Specimen," *Cryobiology*, 1988; 25:67-82.

Hoffmann et al., "Cryosurgery of Normal and Tumor Tissue in the Dorsal Skin Flap Chamber: Part I-Thermal Response," *ASME J. Biomech. Eng.*, 2001; 123:301-309.

Hoffmann et al., "Cryosurgery of Normal and Tumor Tissue in the Dorsal Skin Flap Chamber: Part II-Injury Response," *ASME J. Biomech. Eng.*, 2001; 123:310-316.

Hoffman et al., "Investigation of the Mechanism and the Effect of Cryoimmunology in the Copenhagen Rat," *Cryobiology*, 2001; 41:59-68.

Hoffmann et al., "The Cryobiology of Cryosurgical Injury," *Urology*, 2002; 60(2 Suppl 1):40-49.

Hynsjö et al., "Use of Factorial Experimental Design to Delineate the Strong Calcium- and pH-Dependent Changes in Binding of Human Surfactant Protein-A to Neutral Glycosphingolipids-A Model for Studies of Protein Carbohydrate Interactions," *Anal. Biochem.*, 1995; 225(2):305-314.

Inserte et al., "The Role of $Na^+$-$H^+$ Exchange Occuring During Hypoxia in the Genesis of Reoxygenation-induced Myocardial Oedema," *J. Mol. Cell. Cardiol.*, 1997; 29(4):1167-1175.

Isaacs et al., "Establishment and Characterization of Seven Dunning Rat Prostatic Cancer Cell Lines and Their Use in Developing Methods for Predicting Metastatic Abilities of Prostatic Cancers," *Prostate*, 1986; 9:261-281.

Iyengar et al., "The effects of an iron chelator on cellular injury induced by vascular stasis caused by hypothermiz," *J. Vascular Surg.*, 1990; 12:545-551.

Jackson et al., "Vascular Endothelial Growth Factor (VEGF) Expression in Prostate Cancer and Benign Prostatic Hyperplasia," *J. Urol.*, 1997; 157:2323-2328.

Jacob et al., "An Assessment of Tumor Cell Viability after in Vitro Freezing," *Cryobiology*, 1985; 22:417-426.

Jain, "Analysis of Heat Transfer and Temperature Distributions in Tissues During Local and Whole-Body Hyperthermia," *Heat Transfer in Medicine and Biology*, vol. 2, New York, NY, Plenum Press, 1985, Chapter 16, pp. 3-54.

Jain, "Transport of Molecules in the Tumor Interstitium: A Review," *Cancer Res.*, 1987; 47:3039-3051.

Kane, "Ultrasound-Guided Hepatic Cryosurgery for Tumor Ablation," *Seminars in Interventional Radiology*, 1993; 10:132-142.

Keanini et al., "Optimization of Multiprobe Cryosurgery," *ASME J. Heat Transfer*, 1992; 114:796-801.

Kourosh et al., "Microscopic study of coupled heat and mass transport during unidirectional solidification of binary solutions-I. Thermal analysis," *Int. J. Heat Mass Transfer*, 1990; 33(1):29-38.

Kruuv, "Effects of Pre- and Post-thaw Cell-to-Cell Contact and Trypsin on Survival of Freeze-Thaw Damaged Mammalian Cells," *Cryobiology*, 1986; 23:126-133.

Larese et al., "Antifreeze Proteins Induce Intracellular Nucleation," *Cryo-Letters*, 1996; 17:175-182.

Lewis et al., "Vascular Reactions of the Skin to Injury. Part III.-Some Effects of Freezing, of Cooling, and of Warming," *Heart*, 1926; 13:27-60.

Lim et al., "Growth of an Androgen-Sensitive Human Prostate Cancer Cell Line, LNCaP, in Nude Mice," *Prostate*, 1993; 22(2):109-118.

Love, "The Freezing of Animal Tissue," *Cryobiology*, New York, NY, Academic Press, 1966, Chap. 7, pp. 317-405.

Lovelock, "The Haemoloysis of Human Red Blood-Cells by Freezing and Thawing," *Biochim. Biophys. Acta*, 1953; 10:414-426.

Lovelock, "The Mechanism of the Protective Action of Glycerol Against Haemolysis by Freezing and Thawing," *Biochim. Biophys. Acta*, 1953, 11:28-36.

Lubaroff et al., "Experience with an Animal Model for the Study of Prostatic Carcinoma," *Trans. Am. Assoc. Genito-Urin. Surgeons*, 1978; 69:72-77.

Lubaroff et al., "Immunologic Studies of Prostatic Cancer Using the R3327 Rat Model," *Trans. Am. Assoc. Genito-Urin. Surgeons*, 1979; 70:60-63.

Ludwin, "Survival of Tumor Material after Freezing at -79° C.," *Biodynamica*, 1951; 7(131):53-55.

Manson et al., "Evidence for an Early Free Radical-Mediated Reperfusion Injury in Frostbite," *Free Radical Biology & Medicine*, 1991; 10:7-11.

Marzella et al., "Morphologic Characterization of Acute Injury to Vascular Endothelium of Skin after Frostbite," *Plastic & Reconstructive Surgery*, 1989; 83:67-76.

Mazur, "The Role of Cell Membranes in the Freezing of Yeast and Other Single Cells," *N.Y. Acad. Sci.*, 1965; 125:658-676.

Mazur, "Cryobiology: The Freezing of Biological Systems," *Science*, 1970; 168:939-949.

Mazur et al., "Relative Contributions of the Fraction of Unfrozen Water and of Salt Concentration to the Survival of Slowly Frozen Human Erythrocytes," *Biophys. J.*, 1981; 36:653-675.

Mazur, "Freezing of living cells: mechanisms and implications," *Am. J. Physiol.*, 1984; 247:C125-C142.

McGann et al., "Factors affecting the repair of sublethal freeze-thaw damage in mammalian cells. II. The effects of ouabain," *Cryobiology*, 1974; 11:332-339.

McGann et al., "Factors affecting the repair of sublethal freeze-thaw damage in mammalian cells. I. Suboptimal temperature and hypoxia," *Cryobiology*, 1975; 12:530-539.

McGann et al., "Freeze-Thaw Damage in Protected and Unprotected Synchronized Mammalian Cells," *Cryobiology*, 1977; 14:503-505.

McGrath et al., "An Experimental Comparison of Intracellular Ice Formation and Freeze-Thaw Survival of Hela S-3 Cells," *Cryobiology*, 1975; 12:540-550.

McGrath, "Membrane Transport Properties," *Low Temperature Biotechnology-Emerging Applications and Engineering Contributions*, ASME BED, 1988; 10:273-331.

McHugh et al., "Complications and Postoperative Management," *Percutaneous Prostate Cryoablation*, St. Louis, MO, Quality Medical Publishing, Inc., 1995; title page, pp. 129-135.

Mundth et al., "Treatment of Experimental Frostbite with Low Molecular Weight Dextran," *Journal of Trauma*, 1964; 4:246-257.

Mundth, "Studies on the Pathogenesis of Cold Injury. Microcirculatory Changes in Tissue Injured by Freezing," *Proc. Symp. Arctic Biol. Med. IV. Frostbite*, Feb. 17-19, 1964; 51-72.

Nagle et al., "Cultured Chinese Hamster Cells Undergo Apoptosis after Exposure to Cold but Nonfreezing Temperatures," *Cryobiology*, 1990; 27:439-451.

Neel et al., "Ischemia Potentiating Cryosurgery of Primate Liver," *Ann. Surg.*, 1971; 174:309-318.

Neel et al., "Cryonecrosis of Normal and Tumor-Bearing Rat Liver Potentiated by Inflow Occlusion," *Cancer*, 1971; 28:1211-1218.

Neel, "Cryosurgery for the Treatment of Cancer," *Laryngoscope (Suppl. 23)*, 1980; XC-8(2):31-48.

Ninomiya et al., "Identification of Vascular System in Experimental Carcinoma for Cryosurgery-Histochemical Observations of Lectin UEA-1 and Alkaline Phosphatase Activity in Vascular Endothelium," *Cryobiology*, 1985; 22:331-335.

Onik et al., "Sonographic Monitoring of Hepatic Cryosurgery in an Experimental Animal Model," *Am. J. Roentgenol.*, 1985; 144:1043-1047.

Onik et al., "US Characteristics of Frozen Prostate," *Radiology*, 1988; 168:629-631.

Onik et al., "Percutaneous Transperineal Prostate Cryosurgery Using Transrectal Ultrasound Guidance: Animal Model," *Urology*, 1991; 37:277-281.

Onik et al., "Transrectal Ultrasound-Guided Percutaneous Radical Cryosurgical Ablation of the Prostate," *Cancer*, 1993; 72:1291-1299.

Onik, "Prostate Cryoablation: A Reappraisal," *Percutaneous Prostate Cryoablation*, Quality Medical Publ., Inc., St. Louis, MO, 1995; title page, pp. 1-12.

Onik et al., "Cryosurgical Techniques, Caveats, and Refinements," *Percutaneous Prostate Cryoablation*, Quality Medical Publ., Inc., St. Louis, MO, 1995; title page, pp. 85-128.

Orpwood, "Biophysical and engineering aspects of cryosurgery," *Phys. Med. Biol.*, 1981; 26:555-575.

Pazhayannur et al., "Measurement and Simulation of Water Transport During Freezing in Mammalian Liver Tissue," *ASME J. Biomech. Eng.*, 1997; 119(3):269-277.

Pennes, "Analysis of Tissue and Arterial Blood Temperatures in the Resting Human Forearm," *J. App. Physiol.*, 1948; 1:93-122.

Pham et al., "An in Vivo Study of Antifreeze Protein Adjuvant Cryosurgery," *Cryobiology*, 1999; 38:169-175.

Pollock, et al., "An Isolated Perfused Rat Mesentery Model for Direct Observation of the Vasculature During Cryopreservation," *Cryobiology*, 1986; 23:500-511.

Porter et al., "Radiotherapy and Cryotherapy for Prostate Cancer," Chapter 88, 7th Ed., W.B. Saunders Co., Philadelphia, PA, 1998; title page, publication page, pp. 2605-2626.

Rabin et al., "Experimental Cryosurgery of the Skeletal Muscle of Rabbits' Hindlimbs by Control of the Freezing Rate," *Adv. Heat Mass Trans. in Biotech.*, 1995; BED32:131-132.

Rabin et al., "Analysis of Thermal Stresses Around a Cryosurgical Probe," *Cryobiology*, 1996; 33:276-290.

Rabb et al., "Effect of Freezing and Thawing on the Microcirculation and Capillary Endothelium of the Hamster Cheek Pouch," *Cryobiology*, 1974; 11:508-518.

Rivoire et al., "Hepatic Cryosurgery Precision: Evaluation of Ultrasonography, Thermometry, and Impedancemetry in a Pig Model," *Journal of Surgical Oncology*, 1996; 61:242-248.

Roberts et al., "Biochemical Alterations and Tissue Viability in AT-1 Prostate Tumor Tissue after in Vitro Cryodestruction," *Cryo-Letters*, 1997; 18:241-250.

Robards et al., *Low Temperature Methods in Biological Electron Microscopy*, Elsevier, Amsterdam, Netherlands, 1985; cover page, title page, and table of contents only:8pgs.

Rotnes et al., "Eine Methode Zum Experimentellen Nachweis von Stase Mittels Spezieller Präparate," *Acta Path. Microbiol. Scand.*, 1932; Suppl. 11:162-165.

Rubinsky et al., "Analysis of a Stefan-Like Problem in a Biological Tissue Around a Cryosurgical Probe," *ASME J. Heat Transfer*, 1976; 98(3):514-519.

Rubinsky et al., "A Cryomicroscope Using Directional Solidification for the Controlled Freezing of Biological Material," *Cryobiology*, 1985; 22:55-68.

Rubinsky et al., "The Mechanism of Freezing in Biological Tissue: The Liver," *Cryo-Letters*, 1987; 8:370-381.

Rubinsky et al., "A mathematical model for the freezing process in biological tissue," *Proc. R. Soc. Lond.*, 1988; B234:343-358.

Rubinsky et al., "Effect of Ice Crystal Habit on the Viability of Glycerol Protected Red Blood Cells," *Cryobiology*, Abstracts, 26th Annual Meeting, 1989; 26:580.

Rubinsky et al., "The Process of Freezing and the Mechanism of Damage during Hepatic Cryosurgery," *Cryobiology*, 1990; 27:85-97.

Rubinsky et al., "Cryosurgery: advances in the application of low temperatures to medicine," *Int. J. Refrig.*, 1991; 14:190-199.

Rubinsky, "The Freezing Process and Mechanism of Tissue Damage," *Percutaneous Prostate Cryoablation*, Quality Medical Publ., Inc., St. Louis, MO, 1995; title page, and pp. 49-68.

Saliken et al., "The Evolution and State of Modern Technology for Prostate Cryosurgery," *Urology*, 2002; 60(2 Suppl 1):26-33.

Salimi et al., "Frostbite: Experimental Assessment of Tissue Damage Using Tc-99m Pyrophosphate. Work in progress," *Radiology*, 1986; 161:227-231.

Schmidlin et al., "Measurement and Prediction of Thermal Behavior and Acute Assessment of Injury in a Pig Model of Renal Cryosurgery," *Journal of Endourology* 2001; 15:193-197.

Schüder et al., "Complete shutdown of microvascular perfusion upon hepatic cryothermia is critically dependent on local tissue temperature," *British Journal of Cancer*, 2000; 82:794-799.

Sedzik, "Regression analysis of factorially designed trials-a logical approach to protein crystallization," *Biochim. Biophys. Acta*, 1995; 1251(2):177-185.

Smith et al., "An Estimation of Tissue Damage and Thermal History in the Cryolesion," *Cryobiology*, 1974; 11:139-147.

Smith et al., "Ultrastructure after Cryosurgery of Rat Liver," *Cryobiology*, 1978; 15:426-432.

Smith et al., "A Parametric Study of Freezing Injury in AT-1 Rate Prostate Tumor Cells," *Cryobiology* 1999; 39(1):13-28.

Song et al., "Fibroblast growth factors: An epigenetic mechanism of broad spectrum resistance to anticancer drugs," *Proc. Natl. Acad. Sci. U.S.A.*, 2000; 97:8658-8663.

Steponkus, "Role of the Plasma Membrane in Freezing Injury and Cold Acclimation," *Ann. Rev. Plant Physiol.*, 1984; 35:543-584.

Steponkus et al., "A Contrast of the Cryostability of the Plasma Membrane of Winter Rye and Spring Oat. Two Species That Widely Differ in Their Freezing Tolerance and Plasma Membrane Lipid Composition," *Advances in Low-Temperature Biology*, JAI Press Ltd., London, England, 1993; 2:211-312.

Sullivan et al., "Effect of Inositol and Rapid Rewarming on Extent of Tissue Damage Due to Cold Injury," *Am. J. Phys.*, 1957, 189:501-503.

Tatsutani et al., "Effect of Thermal Variable on Frozen Human Primary Prostatic Adenocarcinoma Cells," *Urology*, 1996; 48:441-447.

Toner et al., "Thermodynamics and kinetics of intracellular ice formation during freezing of biological cells," *J. Appl. Phys.*, 1990; 67:1582-1593.

Toner et al., "Transport Phenomena During Freezing of Isolated Hepatocytes," *AIChE J.*, 1992; 38:1512-1522.

Toner, "Nucleation of Ice Crystals Inside Biological Cells," *Advances in Low-Temperature Biology*, JAI Press, London, England, 1993; 2:1-51.

Trump et al., "Effects of Freezing and Thawing on the Ultrastructure of Mouse Hepatic Parenchymal Cells," *Lab Invest.*, 1964; 13:967-1002.

Watson, "Experience and Perspectives in Prostate Cryosurgery in the United Kingdom," *Percutaneous Prostate Cryoablation*, Quality Medical Publ., Inc., St. Louis, MO, 1995; title page, pp. 155-167.

Yamashita et al., "Enhanced Tumor Metastases in Rats Following Cryosurgery of Primary Tumor," *Gann*, 1982; 73:222-228.

Zacarian, "The Observation of Freeze-Thaw Cycles Upon Cancer Cell Suspensions," *J. Dermatol. Surg. Oncol.*, 1977; 3:173-174.

Zieger et al., Factors Influencing Survival of Mammalian Cells Exposed to Hypothermia. V. Effects of Hepes, Free Radicals, and $H_2O_2$ under Light and Dark Conditions, *Cryobiology*, 1991; 28:8-17.

Zook et al., "Microcirculatory Studies of Frostbite Injury," *Annals of Plastic Surgery*, 1998; 40:246-255.

Han et al., "Thermodynamic Nonequilibrium Phase Change Behavior and Thermal Properties of Biological Solutions for Cryobiology Applications," *J. Biomech. Eng.*, 2004;126(2):196-203.

Han et al., "Direct cell injury associated with eutectic crystallization during freezing," *Cryobiology*, 2004;48:8-21.

Muldrew et al., "Sodium Chloride as an Adjuvant for Cryosurgery," Abstracts, 38th Annual Meeting, *Cryobiology*, International Journal of Low Temperature Biology and Medicine, 2001;43(4):388-389.

Communication and Supplementary European Search Report—Dated Jun. 6, 2007. 3 pages.

* cited by examiner

THERMAL SURGICAL PROCEDURES AND COMPOSITIONS

CROSS-REFERENCE TO RELATED APPLICATIONS

This application claims priority from U.S. Provisional Application Ser. No. 60/457,691, filed Mar. 26, 2003, the entire content of which is incorporated herein by reference.

GOVERNMENT FUNDING

The present invention was made with support from National Institutes of Health under Grant No. R29CA75284. The U.S. government may have certain rights in this invention.

TECHNICAL FIELD

The present invention relates generally to thermal surgical procedures.

BACKGROUND OF THE INVENTION

Thermal surgical procedures, wherein thermal energy is either withdrawn from and/or delivered to a localized region of biological material in an effort to destroy the region of biological material, are known in the art and have been shown to be an effective treatment of disease, particularly in instances wherein a patient is unwilling or unable to undergo another form of surgery. A thermal surgical procedure may include, for example, a cryosurgical procedure in which thermal energy is removed from biological material to cool and/or freeze the biological material in an effort to destroy it. Such procedures have been routinely used to treat malignancies on the surface of the body and is also used for treating and managing malignancies of internal organs, such as kidney and prostate. Also, a thermal surgical procedure can include a procedure in which thermal energy is added to biological material to heat the biological material in an effort to destroy it. The destruction of biological material may or may not result in ablation of some or all of the biological material. Thermal surgical procedures are useful in treating diseases of various tissues, including, for example, carcinomas of the liver, kidney, and prostate. These techniques are advantageous in that they have the potential for less invasiveness and lower morbidity as compared with surgical excision.

Thermal surgical procedures involving delivery of thermal energy to increase the local temperature of biological material above the physiological temperature is known to be an effective treatment for eliminating malignant tissue. Typical temperatures for thermal surgical procedures involving the delivery of thermal energy are at or above 50 degrees Celsius (° C.). Typically, the biological material is heated to elevated temperatures and is maintained at these temperatures for an interval of several minutes.

Additionally, it is known in the art that freezing biological materials is an effective method for controlling and destroying the cells and tissues of, for example carcinomas of various tissues and organs. Cryosurgical techniques, in combination with monitoring techniques, such as ultrasound and MRI, have provided effective treatment of a number of internal organs, including liver, prostate, and kidneys. Results of cryosurgery involving carcinomas in kidneys suggest that this may prove a useful technique, particularly for small renal cell carcinomas. Cryosurgical procedures typically reduce the temperature of the biological material to temperatures close to or below the temperature at which the biological material will freeze, often below 0° C. and as low as −20 to −60° C. Typically the biological material is cooled to and maintained at these temperatures for an interval of minutes.

Nonetheless, there exists clinical evidence of recurrence of disease in thermal surgically treated patients. This result may be due to the initial challenge of treating the entire diseased tissue. For example, in current thermal surgical procedures it is prudent to take a sufficient surgical margin around diseased tissue to ensure all of the malignant tissue is removed or destroyed. This often involves freezing or heating beyond a tumor and invading surrounding normal tissue. However, care must be taken to not invade too far beyond the diseased tissues, particularly when treating biological material near healthy sensitive tissues. In particular, when treating prostate cancers, which occur principally in the peripheral zone of the prostate near a number of sensitive structures, such as the rectum, bladder, external sphincter, and the cavernosal nerves, a surgeon must be careful to spare the surrounding tissues from injury. This is particularly important in treating the prostate where overfreezing into the areas of the rectum and urethra can cause rectal and urethral fistulas. On the other hand, if a surgeon is too conservative and underheats or underfreezes affected tissues, the disease may not be effectively treated and the likelihood of recurrence of the disease increases.

There is a need in the art, therefore, to improve the clinical application of thermal surgical procedures, including effectively monitoring of the heating or freezing of the biological material to more effectively predict the zone of injury, reproducibly creating and enhancing cell death within the heat treated area or the cryolesion, and improving definition of the edge of the heat treated area or the cryolesion to improve the effectiveness of the kill zone while protecting adjacent normal tissues.

SUMMARY OF THE INVENTION

The present invention provides a composition, method, system, and/or kit for use in a thermal surgical procedure. As used herein thermal surgical procedures generally include, but are not limited to, surgical procedures in which thermal energy is either withdrawn from and/or delivered to a localized region of biological material in an effort to destroy at least a portion of biological material.

The compositions of the present invention include one or more compounds that can effectively induce an inflammation response in biological materials involved in the thermal surgical procedure. A "compound" as used herein, may include a single constituent or a combination of two or more constituents. Furthermore, a "composition" as used herein may include only one compound or combination of two or more compounds.

Biological materials that may be treated using the compositions, methods, and systems of the present invention include, but are not limited to, cells, tumor cells, tissue, tumor tissues, tissues of internal organs such as liver tissue, prostate tissues, breast tissue, and kidney tissues. In addition, biological materials may also include, but are not limited to vascular tissues, gastrointestinal tissues, muscle tissues, including myocardium, tissues of the skin, and connective tissues. Combinations of these biological materials in situ are possible, and treatment of some biological materials to the exclusion of others is also contemplated.

The present invention may be used in the treatment of various cancers and/or tumors such as, but not limited to, prostate cancer, liver cancer, kidney cancer, breast cancer, uterine fibroids, as well as any other tumor or tissue where thermal surgical procedures have typically been used or which may be found useful in the future. The present invention may also be useful in the treatment of benign prostatic hypertrophy (BPH), or treatment of stenosis of the urethra. In addition, the present invention may also be useful in treating any number of autoimmune and chronic inflammatory disorders, where the associated tissues involved in the disorder are predisposed to injury from cooling or heating. Examples include, but are not limited to, rheumatoid arthritic syndrome, emphysema, pulmonary hypertension and cardiac failure, Crohn's disease, neurological disorders that display neuroinflammatory disease, ulcerative colitis, and other known autoimmune diseases.

In addition, the present invention may also be useful in any number of interventional procedures that are currently used to treat individuals. For example, the present invention may be useful in procedures that utilize cooling or heating to destroy biological materials. Thus, the present invention may be used in conjunction with thermal surgical procedures performed on myocardial tissue for treating rhythm irregularities of the heart. Further, the present invention may be used in preventing restenosis of arteries treated with angioplasty, atherectomy, or other procedures for opening occlusions in the vasculature.

In one aspect, the present invention includes a method of performing a thermal surgical procedure, wherein the method includes: identifying biological material to undergo the thermal surgical procedure; contacting the biological material with an inflammation inducing composition, wherein inflammation is induced in at least a portion of the identified biological material; and adjusting the temperature of the identified biological material, wherein at least a portion of the biological material is destroyed after undergoing the thermal surgical procedure. The temperature may be adjusted above a physiological temperature of the biological material, a thermosurgical procedure, or the temperature may be adjusted to below a physiological temperature, as in a cryosurgical procedure. It is contemplated that a thermal surgical procedure may also include both a thermosurgical procedure and a cryosurgical procedure, either on the same identified biological material with the procedures performed at separate times, or on separate sites of the identified biological material.

In another aspect, the present invention includes a composition that includes at least one compound effective for inducing an inflammatory response in biological material that is identified to undergo a thermal surgical procedure. The composition may include a single constituent as the active ingredient, or may include a combination of active ingredients. Furthermore, the composition may also include such optional constituents as a physiological carrier and/or a buffering agent.

In a further aspect, the present invention provides a method of performing a thermal surgical procedure for biological material, wherein the thermal surgical procedure may be a thermosurgical procedure, a cryosurgical procedure, or any combination thereof. The thermal surgical procedure includes: identifying biological material to be treated prior to a thermal surgical procedure; contacting the biological material with an inflammation inducing composition for a time, amount and type effective to induce inflammation in at least a portion of the biological material, wherein inflammation is induced in at least a portion of the identified biological material; and adjusting the temperature of the identified biological material, wherein at least a portion of the biological material is destroyed after undergoing the thermal surgical procedure.

The present invention additionally provides a system for inducing inflammation in biological material identified to undergo a thermal surgical procedure. This system generally includes: a composition including at least one compound effective for inducing inflammation in at least a portion of the biological material; and means for delivering the composition to a least a portion of the biological material. The composition may include a single active ingredient or more than one active ingredient, and may further include optional constituents, such as a pharmaceutically acceptable carrier and/or a buffering agent.

In an additional aspect, the present invention provides methods of treating diseases, such as cancer. A method of treating cancer is disclosed which includes: identifying a localized region of a mammal comprising biological material further including cancer; providing to at least a portion of the biological material a composition comprising as an active ingredient at least one compound for a time, amount and type effective to induce inflammation in at least a portion of the biological material, thereby providing inflamed biological material; and applying a thermal surgical procedure to at least a portion of the inflamed biological material. The thermal surgical procedure may be a thermosurgical procedure, a cryosurgical procedure, or a combination thereof.

Additional diseases may be treated by the methods and compositions of the present invention. For example, the present invention includes a method of treating a disease that includes: identifying a localized region of a mammal comprising biological material typical of the disease; providing to at least a portion of the biological material a composition comprising as an active ingredient at least one compound for a time, amount and type effective to induce inflammation in at least a portion of the biological material, thereby providing inflamed biological material; and applying a thermal surgical procedure to at least a portion of the inflamed biological material.

The present invention further discloses a kit for use in a thermal surgical procedure. Such kit includes, generally: a thermal surgical probe adapted to transfer thermal energy; and a composition comprising at least one compound effective for inducing an inflammatory response in biological material identified to undergo a thermal surgical procedure.

The above summary of the present invention is not intended to describe each embodiment or every implementation of the present invention. Advantages, together with a more complete understanding of the invention, may become apparent and appreciated by referring to the following detailed description of illustrative embodiments taken in conjunction with the accompanying drawings.

DETAILED DESCRIPTION OF ILLUSTRATIVE EMBODIMENTS

In the following detailed description of certain illustrative embodiments, reference is made to drawings that form a part hereof, and in which are shown by way of illustration, certain embodiments through which the invention may be practiced. It is to be understood that other embodiments may be utilized and processing steps/structural changes may be made without departing from the scope of the present invention.

As will be discussed below, the present invention provides methods, compositions, and systems for use in treating biological materials including, for example, cells, tissues, and combinations thereof, with a thermal surgical procedure. The present invention generally includes an inflammation inducing composition that can be used to treat the biological material that is the subject of the thermal surgical procedure, wherein the biological material to undergo a thermal surgical procedure may be identified, in whole or a portion thereof, and is treated with an inflammation inducing composition of the present invention for a time, in an amount, and of a type effective to induce at least some inflammation in at least a portion of the identified biological material. The present invention further includes methods and systems for inducing such inflammation. The inflammation inducing composition of the present invention can be used to induce an inflammatory response in the biological material, where the induced inflammatory response may provide for an enhancement of destruction of the biological material during the thermal surgical procedure.

The methods and compositions of the present invention may be useful in treating several diseases, including cancer. Cancers that may potentially be treated by the present methods and compositions include, but are not limited to, cancers of internal organs, such as prostate, liver, and kidney, cancers of bone and cartilage, skin cancer, oral cancer, musculoskeletal cancers, breast cancer, gynecological cancers including uterine fibroids. Other diseases that may benefit from the methods and compositions of the present invention include, for example, benign prostatic hypertrophy, stenosis of the urethra, rheumatoid arthritic syndrome, emphysema, pulmonary hypertension, cardiac failure, Crohn's disease, neurological disorders displaying neuroinflammatory disease, ulcerative colitis, and gynecological disorders.

Inflammation is understood herein to typically involve a complex series of events which may include, but is not limited to, dilatation of arterioles, capillaries and venules, with increased vessel permeability and blood flow, exudation of fluids through the vessel walls, including plasma proteins and leucocytic migration into the inflammatory focus. Further, on a molecular level adhesion molecules are typically upregulated in endothelial cells which slow down (by rolling) and capture (by adhesion) leucocytes to the vessel walls in the area of inflammation.

Without wishing to be bound by any particular theory, it is believed that an induced inflammatory response in biological materials intended to undergo a thermal surgical procedure may augment the effectiveness of that procedure. It is further believed that by controlling the extent and degree of the induced inflammatory response in the biological material, the degree to which the thermal surgical procedure will be successful may be significantly influenced. Using compounds that, for example, induce non-destructive inflammation in biological material provides beneficial changes in the effectiveness of thermal surgical procedures as compared to untreated biological material. Thus, the present invention provides improvements in typical thermal surgical procedures by providing what is believed to be a controllable and reproducible technique to accentuate the injury and death of biological material undergoing the thermal surgical procedure.

Thermal surgical procedures have been shown to be effective treatment modalities for several tumor tissues. For example, cryosurgical procedures are known to be effective treatments for eliminating malignant tissue. In cryosurgical procedures, thermal energy is removed from at least a portion of the biological material so as to decrease the local temperature below a physiological temperature of the biological material. A physiological temperature of the biological material is generally understood to be that temperature at which the physical mechanisms of living organisms and/or parts thereof are able to function. Cryosurgical procedures reduce the temperature of the biological material to temperatures close to and/or below the temperature at which the biological material will freeze. Typical temperatures for cryosurgical procedures include those at or below 0° C., and may further include temperatures at or below approximately −20° C., going down to at or below −60° C. The biological material may be cooled to and maintained at these temperatures for, e.g., an interval of minutes, or any other suitable period of time, to ensure effectiveness of the treatment.

While in a cryosurgical procedure it may be preferred to take a sufficient surgical margin around the malignant tissue to ensure that all tumor tissue has been removed or destroyed, often requiring freezing beyond the tumor into normal tissue, the present invention is believed to reduce the potential side effects of normal tissue damage during cryosurgery, and to maximize the tumor destruction at the edge of the cryosurgical ice ball, strategies to both protect (e.g., normal) and sensitize (e.g., tumor) cells to freezing. Protecting and/or sensitizing tissues from temperatures experienced within the ice ball may allow surgeons to functionally increase the surgical margin while decreasing damage to surrounding tissues. Also, increasing the efficiency of tissue destruction within the ice ball may increase the confidence that an increased number of, e.g., tumor cells are killed near the periphery of the tissue of interest while decreasing the chances of over-freeze damage into adjacent normal tissues, such as, e.g., the rectum, in prostate cryosurgery.

It is also believed that the present invention may provide for better assessment of the actual location of cell and tissue death in the ice ball formed during a cryosurgical procedure. Assessment of this location can be based in part on the region of biological material undergoing an inflammatory response induced by the use of the inflammation inducing composition of the present invention. Use of the inflammation inducing composition of the present invention may allow for a greater percentage of cell and/or tissue destruction during the cryosurgical procedure.

Thermal surgical procedures that deliver thermal energy to biological material, understood herein as "thermosurgical procedures" are also known to be effective treatments for eliminating malignant tissue. In these thermosurgical procedures, thermal energy is supplied to at least a portion the biological material so as to increase the local temperature above a physiological temperature of the biological material. For example, typical temperatures for these thermosurgical procedures generally include those at or above 50° C. It is noted that by the methods and composition of the present invention, it may be possible to perform effective thermosurgical procedures at temperatures below 50° C., such as temperatures no greater than about 40° C., thereby preventing injury to adjacent tissues. The biological material may be heated to and maintained at these temperatures for, e.g., an interval of minutes, or any other suitable period of time, to ensure effectiveness of the treatment.

As with cryosurgery, it is typically considered to be beneficial to take a sufficient surgical margin around the biological material of interest through the use of the heat to ensure that all the biological material of interest has been removed or destroyed. However, taking a sufficient margin around the biological material typically requires heating beyond the biological material of interest into normal tissue. To minimize the potential side effects of normal tissue damage during a heat-delivering thermal surgical procedure, and to maximize the destruction at the edge of the heated biological tissue, strategies to both protect (e.g., normal) and sensitize (e.g., tumor) cells to heating are also desirable.

The present invention is believed to sensitize tissues to and/or protect tissues from temperatures experienced at either the edge of the ice ball or the edge of the heated biological material. As a result, surgeons performing thermal surgical procedures according to the present invention could potentially functionally increase the surgical margin while decreasing damage to surrounding tissues by increasing the efficiency of tissue destruction at the edge of the ice ball or the edge of the heated biological tissue and may also obtain better assessment of the actual location of cell and tissue death in the ice ball formed during a cryosurgical procedures and/or the actual location of cell and tissue death at the edge of the heated biological tissue formed during the thermal surgical procedure.

Improvement of the assessment of the actual location of cell and/or tissue death, according to the present invention, is believed to be based in part on the region of biological material undergoing an inflammatory response induced by the use of the inflammation inducing composition of the present invention. Use of the inflammation inducing composition of the present invention is believed to provide a greater percentage of cell and/or tissue destruction during the thermal surgical procedures contemplated by the present invention.

Generally, the compositions of the present invention may be used in a localized region of a mammal involved in the thermal surgical procedure. Typically, the composition includes as an active ingredient at least one compound effective to induce at least some inflammation in at least a portion of the biological material of interest, such as any native or artificial tissue of a mammal, where the at least one compound can be effective to induce inflammation in at least a portion of the localized region of the native or artificial tissue of the mammal.

A composition of the present invention typically induces a non-destructive inflammation within the biological material of interest, either localized to the entire region of the thermal surgical site or localized to one or more portions of the thermal surgical site, prior to, during, and/or after the thermal surgical procedure. For example, a composition of the present invention may be used to induce an inflammatory response in a localized region of the biological material prior to or concurrent with a thermal surgical procedure. Furthermore, a composition of the present invention may be used in a localized region of a mammal to treat biological material, for a time, and in an amount and using a type of composition effective to induce inflammation in the material, that has previously been identified and has undergone a thermal surgical procedure.

While not wishing to be bound by a particular theory, it is believed that the composition of the present invention may induce this non-destructive inflammation by altering the behavior of vascular endothelial cells present in biological material. In particular, it is believed that the inflammation induced by the compositions of the present invention may injure the microvasculature of the biological tissue prior to the thermal surgical procedure. It is also believed that this induced inflammatory injury may precondition the microvasculature so that it "shuts down" after the thermal surgical procedure. In combination with the thermal surgical procedure, it is believed that the use of the composition of the present invention may provide a more effective destruction of the biological material undergoing a thermal surgical procedure by enhancing the effects of the procedure than would be provided by the thermal surgical procedure performed alone without benefit of inflaming the biological material.

Without being held to any particular theory, it is believed that through an understanding of the nature of cell injury, it may be possible to accentuate the mechanisms of injury utilizing targeted molecular adjuvants such as those described herein. It is further believed that two biophysical changes that occur in cells during freezing, osmotic dehydration of cells and intracellular ice formation (IIF) may be linked to cell injury. At low cooling rates, as the freezing propagates extracellularly, the solute concentration outside the cell begins to rise, causing osmotic dehydration of the cells. As the solutes become concentrated within the cells, the high concentration of solute has been hypothesized to injure the cell in several ways including damage to the enzymatic machinery and destabilization of the cell membrane.

The second biophysical response, IIF, is believed to occur when the cooling rate is sufficiently rapid to trap water within the cell. In this case, the cell cannot osmotically equilibrate with the extracellular space. As a result, the cytoplasm cools and ice ultimately nucleates within the cell, the ice crystals causing injury to the organelles and membranes.

Damage due to solute effects is believed to typically happen at relatively low cooling rates when the cells have sufficient time to dehydrate substantially completely. IIF damage, on the other hand, is believed to typically occur at relatively high cooling rates, when the water is trapped inside the cells. This results in an "inverse U curve" of cell viability with low viability at extremely high and low cooling rates, and high viability at cooling rates between the extremes. This cooling rate behavior is highly cell-type dependent with the cooling rate that yields maximum viability (i.e. the top of the inverse U) ranging over many orders of magnitude 1-1000° C./minute.

Cellular injury mechanisms may depend on the thermal history that a cell experiences during freezing. This thermal history is defined by four thermal parameters: cooling rate (CR), end (or minimum) temperature (ET), time held at the minimum temperature (hold time, HT), and thaw rate (TR), all of which have been linked to injury. It has been found in AT-1 tumor cells that ET and HT are the most injurious in cell suspensions. However, each cell type investigated typically has a unique thermal threshold where AT-1 cells can survive to −80° C. and ELT-3 uterine fibroid cells can survive only to −30° C. with other thermal parameters being similar, and, as indicated above, if the rates of cooling and heating (CR, TR) are sufficiently high, cell damage irrespective of the ET and HT may be obtained.

Treating biological material by contacting the material with the compositions of the invention, thereby inducing inflammation in the localized region of the material, is also believed to cause various changes in the biological material. For example, it is believed that such treatment may be effective in changing a destruction point of the biological material in a localized region of a mammal. As used herein, the "destruction point" is understood to mean the temperature at which the biological functions of the biological material undergoing the thermal surgical procedure are rendered irreversibly inoperative, either during the procedure or shortly thereafter, preferably within three days or less, more preferably within two days or less, even more preferably within one day or less, and still more preferably within 12 hours or less of the procedure. In some instances, the functions of the biological material may be rendered irreversibly inoperative within 2 hours or less of the procedure, and preferably within one hour or less of the procedure. In other words, the destruction point is the temperature, the hold time at a given temperature, and/or the rates of heating and/or cooling at which cell death results in the localized region of the biological material. These temperatures can include those that are below normal physiological temperatures and those that are above normal physiological temperatures, and the destruction point is variable, depending upon the biological materials of interest.

Without being held to a particular theory, it is believed that so treating the biological material induces more effective killing at the edge of the treated area, such as through endothelial injury and microvascular shut-down post freeze at the edge of the ice ball in a cryosurgical procedure. One may be able to visualize the edge of the ice ball using monitoring techniques such as NMR, CT, or ultrasound. Therefore, by using an inflammatory agent to provide destruction of biological material out to the edge of the ice ball, it may be possible to visualize the region of injury intraoperatively rather than post-operatively in follow-up, thus potentially increasing the control and effectiveness of the thermal surgical technique.

The inflammatory inducing compounds of the present invention are considered herein to be adjuvants that enhance the thermal surgical procedure. As used herein, to "enhance a thermal surgical procedure" is considered to include, but not be limited to, increasing a percentage of cell death in the localized region of the biological material within a given time period as compared to untreated regions of the biological material.

Alternatively, a thermal surgical procedure may be enhanced by attempting to control the injury. This may be accomplished in a cryosurgical procedure, for example, through the use of any of a class of compounds used to diminish the injury, rather than to augment it. These compounds are cryoprotective agents and include, for example, glycerol, dimethylsulfoxide, various sugars, various alcohols, and various polymers such as PVP and HES, may enhance the surgical procedure by, in essence, "sculpting" the ice ball from the outside rather than controlling it from within the ice ball.

The compositions of the present invention include at least one compound, and may include more than one of any of a number of compounds capable of inducing some degree of inflammation in at least a portion of the treated (i.e., contacted) biological material of a mammal, wherein the material is identified to undergo a thermal surgical procedure. For example, the compounds may include, but are not limited to, one or more viruses, one or more bacteria, ethanol, cytokines such as Tissue Necrosis Factor-alpha (TNF-alpha) or truncated versions of TNF-alpha, bacterial lipopolysaccharides (LPS), interleukins such as IL-1 beta and IL-8, chemokines which recruit white blood cells, oxygen-free radicals, and combinations thereof.

Selection of the one or more inflammatory inducing compounds may take into consideration the individual effects and traits of the compound. TNF-alpha, for example, is known to promote inflammation, endothelial injury, and apoptosis, and may be used alone or in combination with other compounds to provide the desired benefit. TNF-alpha is produced by a number of different cell types, macrophages, tumor and stromal cells and is thought to be responsible for manifestation of autoimmune and chronic inflammatory disorders. As discussed hereinbelow, in one embodiment of the invention, TNF-alpha may be directly injected into the biological material of interest (e.g. a tumor) in order to increase the efficacy of the thermal surgical procedure. Alternatively, in a further embodiment, cells that produce TNF-alpha might be directed to, or injected into, the biological material of interest to increase the efficacy of the thermal surgical procedure through inflammation of the biological material.

There are various methods for delivering the composition to the biological material of interest, such methods being an issue of selecting an appropriate drug delivery system. One method includes the addition of one or more carriers, particularly carriers that may have specific receptors for the tumor or tissue of interest. Thus, the inflammation inducing compositions of the present invention may optionally include a pharmaceutically acceptable carrier for delivery to the material of interest, which carrier may also optionally have specific receptors for the tumor or tissue of interest.

As used herein, a pharmaceutically acceptable carrier may include, but is not limited to, liquid solvents in which the inflammation inducing compound can be at least partially suspended and/or diluted, such as a saline solution, and any other carrier which may provide for direct interstitial injection in liquid suspension, IV or IP injection, impregnation of the composition into microbeads or nanobeads to be injected locally or systemically and then targeted, gelfoam, retroviral DNA injections (gene therapy), etc., and combinations thereof.

Pharmaceutically acceptable carriers may also optionally include buffering agents, as are known, to ensure the resulting inflammation inducing composition has a pH value within a range acceptable for physiological use. Such agents may include, but are not limited to phosphate buffered solutions.

The inflammation inducing compositions of the present invention may also include further components to provide additional benefits. For example, additional components may include, but are not limited to, a composition to further enhance cell and tissue destruction by cryosurgery. U.S. Pat. No. 5,654,279 to Rubinsky et al. provides one example of possible additional additives. An additional example includes additives that may provide for eutectic freezing in the biological material 12 as provided in U.S. Pat. No. 10/461,763 entitled CRYOSURGERY COMPOSITIONS AND METHODS, filed on Jun. 13, 2003. In addition, chemotherapeutic agents can also be introduced with the inflammation inducing composition.

As discussed in more detail below, the location and/or extent to which the inflammation inducing composition may be infused into the tissue can be monitored through any number of known techniques. The inflammation inducing compositions may, therefore, optionally include compounds to assist in visualization and monitoring. For example, compounds and/or solutions that may enhance ultrasonic imaging, fluoroscope, MRI, impedance technique (e.g., U.S. Pat. No. 4,252,130 to Le Pivert), etc., can be added to the inflammation inducing composition to allow for visualization of the location of the inflammation inducing composition. Examples include, but are not limited to, contrast agent added with salt (i.e., hypaque) and/or the inflammation inducing compounds, salt and/or the inflammation inducing compounds tagged with a fluorescent marker, ultrasound contrast agents, and use of an impedance metric device to see how impedance changes locally with infusion.

The time interval for treating the biological material with the composition of the present invention prior to performing a thermal surgical procedure can range from, e.g., a matter of minutes, hours, or days, depending on the composition and biological material of interest, and the required time interval is measured according to the effectiveness of the kill. However, it is currently believed that improved effects may be provided if at least about one hour or more elapses between delivery of the composition to the biological material and the thermal surgical procedure. As an example, it may be possible to use a four (4) hour time interval for treating biological material with the composition of the present invention prior to performing the thermal surgical procedure. This time may, however, change depending upon any number of factors, including but not limited to, the type and location of the biological material, the inflammatory composition used (and/or its delivery system), and the existing physiological state of the biological material.

Without being held to any particular theory, it is believed that the inflammatory response typically should be sufficiently activated within the endothelium of the microvasculature to give the augmented injury response after cryosurgery or thermosurgery. The inflammatory response as measured by adhesion molecule production within endothelium (VCAM and ICAM) may typically take several hours to peak. However, in certain instances it may be true that much shorter times, such as on the order of minutes, will provide the desired response.

The methods of the present invention include methods of performing a thermal surgical procedure in which the biological material identified to undergo the procedure is contacted with an inflammation inducing composition of the present invention, and the temperature of the biological material is adjusted. The temperature is adjusted such that the material is either cooled to below or heated to above a physiological temperature to destroy at least a portion of the material. The composition selected is a type such that, for a specified time and amount of the composition, inflammation is induced in at least a portion of the biological material, and such inflammation is induced. Such treatment of the material (i.e., contact with the composition) may occur either during the surgical procedure, before the procedure, after the procedure, or any combination thereof.

Treatment of the biological material is considered to include, but not be limited to, one or a combination of means for delivering the composition to at least a portion of the identified biological material. Such delivery means may include, but not be limited to, introduction of the composition into one or more locations of the biological material through the use of hypodermic needles, introduction via of one or more needles integrated into or attached to a cryoprobe, introduction via diffusion, and introduction via iontophoresis (or any other use of electric fields to drive solution flow in tissues), direct interstitial injection in liquid suspension, IV or IP injection, impregnation of the composition into microbeads or nanobeads to be delivered locally or systemically and then targeted, retroviral DNA injections (gene therapy), etc., and combinations thereof.

Alternatively, the delivery means could involve incorporation of the composition into a gel or foam for topical use, or incorporated into an implantable material to be used before or after the thermal surgical procedure, for example, a gelfoam, a tissue engineered collagen, fibrin based product, etc.

Biological materials to be treated according to the methods and systems of the present invention typically have a destruction point, that is, a temperature, or the hold time at a given temperature, and/or the rates of heating and/or cooling at which cell death results in the localized region of the biological material, with the temperature typically above or below physiological temperatures, that is, temperatures at which the biological functions of the biological material undergoing the thermal surgical procedure are rendered irreversibly inoperative (i.e., cell death in the localized region of the biological material). Without being held to any particular theory, it is believed that the present invention operates, at least in part, to change the destruction point of, for example, a localized region of a mammal that includes biological materials identified to undergo a thermal surgical procedure.

The present invention is believed to provide improved assessment of the actual location of cell and/or tissue death in identified biological materials. Such assessment is aided through the use of known monitoring techniques that may locate and/or determine the extent to which the inflammation inducing composition has been infused into the tissue including, for example, ultrasonic imaging, fluoroscope, MRI, and impedance techniques, particularly when used in conjunction with a composition including an imaging enhancing compound such as vascular perfusion contrast agents. Thus, by being able to visualize, for example, the edge of an ice ball during a cryosurgical procedure, the edge of the injury during the procedure may be monitored during the procedure, providing improved intraoperative imaging and injury assessment.

The present invention further provides systems for inducing inflammation in at least a portion of biological material intended to undergo a thermal surgical procedure that includes a composition of the present invention and means for delivering the omposition to the biological material. Such delivery means may include, for example, delivery of the composition through a catheter (e.g., through a lumen, in a balloon or other chamber positioned at a desired location, etc.), delivery via a needle, and delivery via a thermal surgical probe adapted to transfer thermal energy, such as, e.g., a cryoprobe.

The composition may be delivered either directly to the site of the thermal surgical procedure, or may be delivered to another location, such as, e.g., a site adjacent to the location of the thermal surgical procedure, or may be delivered systemically when appropriate. Further, the inflammation inducing composition may be delivered to the biological material before, during, and/or after a thermal surgical procedure.

Systems of the present invention may further include the use of a thermal energy transfer means that provides thermal energy to biological material (a heat source) or that removes thermal energy from biological material (a heat sink). Such means may include, for example, thermal surgical probes, catheters, implantable devices, etc. An effective means of providing and/or removing thermal energy in the methods and systems of the present invention may be a thermal surgical probe, wherein the probe is effective for either removing thermal energy from or supplying thermal energy to, depending on the type of thermal surgical procedure contemplated, at least a portion of the biological material of interest at a rate to provide heating or cooling, resulting in at least partial destruction of biological material at the location of the thermal surgical procedure. Such probes may include, for example, catheters, hollow needles, cryoprobes, implantable devices, etc.

The present invention may include a kit for use in a thermal surgical procedure. The kit may include a thermal surgical probe that is adapted to transfer thermal energy as appropriate, either by removing thermal energy for use in a cryosurgical procedure, or by supplying thermal energy, for use in a thermosurgical procedure. The kit preferably includes a composition that includes at least one compound effective for inducing an inflammatory response in biological material identified to undergo a thermal surgical procedure. Such compositions may include one or more of compounds that are selected from the group of at least one virus, at least one bacterium, ethanol, cytokines, interleukins, chemokines, oxygen-free radicals, bacterial lipopolysaccharides, and any combination thereof. If a cytokine is selected for use, it may be preferred that the cytokine used is TNF-alpha, truncated versions of TNF-alpha, and any combination thereof. If an interleukin is selected for use, it may be preferred that the interleukin used is IL-beta, IL-8, and any combination thereof. The composition may further include an optional pharmaceutically acceptable carrier and/or any of the optional constituents previously discussed. The probe that is used is any that may be adapted for use in a thermal surgical procedure such as, but not limited to, a catheter, a hollow needle, a cryoprobe, an implantable medical device, etc.

Figure 1:
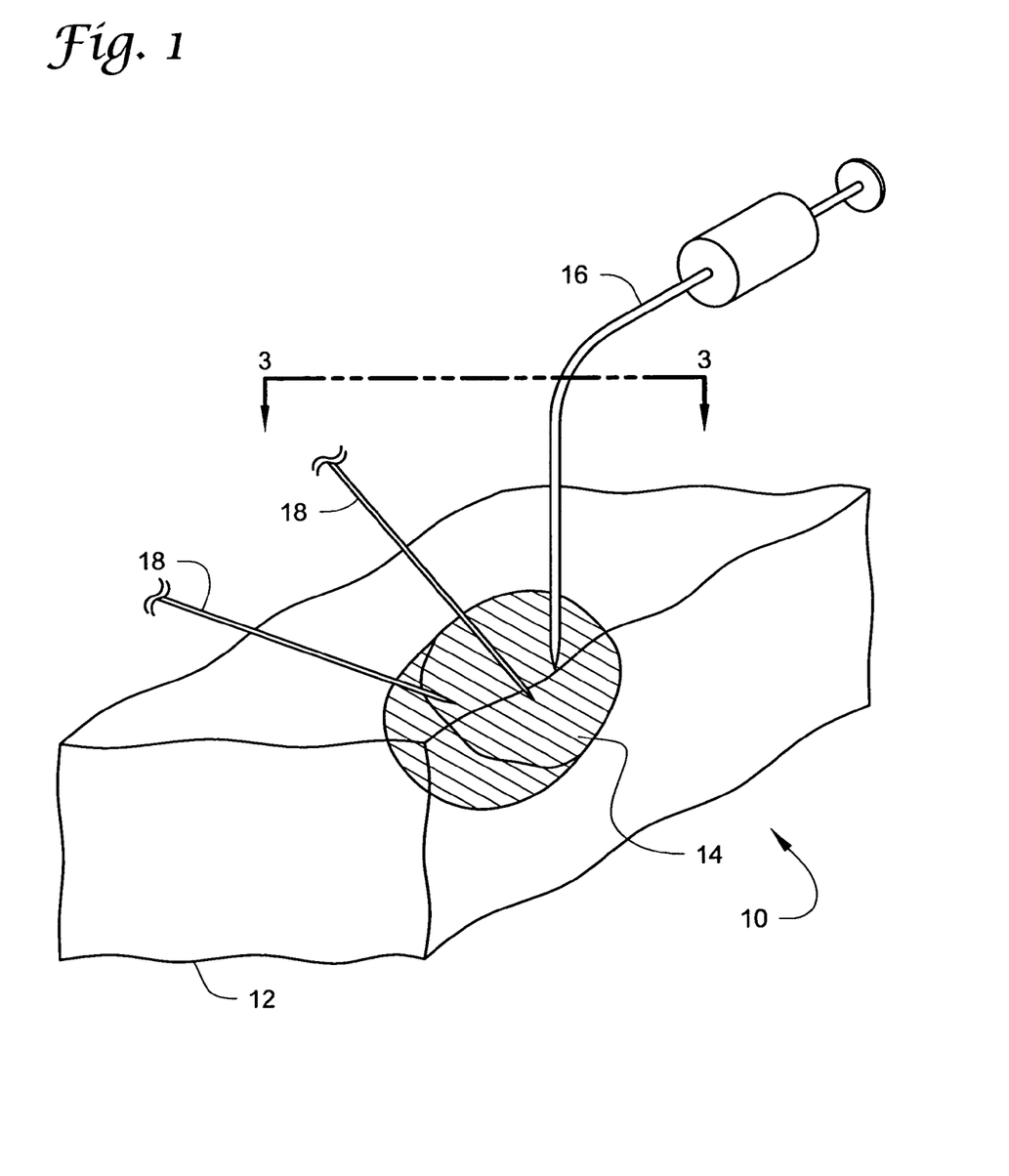
FIG. 1 shows one embodiment of a system according to the present invention.

As an example, FIG. 1 shows one possible embodiment of a system 10 according to the present invention for inducing inflammation in biological material 12 that includes a portion 14 that has been identified to undergo a thermal surgical procedure. As discussed herein, the biological material 12 can include a tissue, including cells, intended to undergo, at least in part, a thermal surgical procedure. The portion 14 of biological material 12 can have a similar cell and/or tissue structure as the surrounding segment of biological material 12. Alternatively, the portion 14 can have one or more morphologically distinct cell and/or tissue structures as compared to the remaining segment of the biological material 12. In one example, the portion 14 can be a tumor.

The inflammatory state of the portion 14 of the biological material 12 can be changed relative to the remaining segment of the biological material 12 through the use of the inflammatory inducing composition of the system 10 of the present invention. The biological material 12 may be treated with the inflammation inducing composition of the present invention for a time, in an amount and of a type effective to induce inflammation in at least a portion of the identified biological material. In one example, the inflammation inducing composition can be one or more of the compounds for inducing an inflammatory response as discussed herein.

The portion 14 of the biological material 12 to be treated with the inflammation inducing composition as a part of the thermal surgical procedure may be identified by any number of known techniques. For example, tumor structures may be identified through tissue structure, biological markers, ultrasound, or any number of other techniques. Furthermore, the location and/or extent to which the inflammation inducing composition has been infused into the tissue (e.g., the portion 14 in FIG. 1) can also be monitored through any number of techniques, and one or more identification and/or monitoring techniques may be used as required.

Once identified, the inflammation inducing composition can be delivered to the portion 14 of the biological material 12. In one possible embodiment, the composition can be delivered through the use of delivery device, such as, e.g., a catheter 16. In general, the catheter 16 includes a lumen, where the inflammation inducing composition can move through the lumen of the catheter 16 and into the biological material 12 in which the inflammatory response is desired. The catheter 16 of the present invention may also include a needle at a distal end of the catheter 16 for delivering the inflammation inducing composition. Alternatively, the catheter 16 can further include a trocar in the lumen of the catheter 16 to facilitate delivering a portion of the catheter 16 to the biological material 12 in which the inflammatory response is desired. U.S. Pat. No. 5,807,395 provides some examples of catheters 16 that may be suitable for injecting the inflammation inducing composition of the present invention.

The system 10 may also include one or more probes 18, where the probes 18 can remove and/or deliver thermal energy from the location for thermal surgical procedure at a rate sufficient to cause biological material 12 at the location for thermal surgical procedure to undergo cooling or heating. In one embodiment, heat may be removed at a rate sufficient to cause cooling of the tissue surrounding the probe at a 1-100° C. per minute rate. In an additional embodiment, thermal energy may be supplied at a rate sufficient to cause heating of the tissue surrounding the probe at a 1-100° C. per minute rate. In some embodiments, the catheter 16 (or other device) used to deliver the inflammation inducing composition may also be used to deliver or remove thermal energy, as discussed herein.

Other rates are also contemplated in the methods and systems of the present invention, depending on the circumstances of use. During a cryosurgical procedure, for example, intracellular ice formation may occur at higher rates, typically greater than about 30° C./minute, more typically greater than about 50° C./minute. This mechanism of injury may occur proximate the cryosurgical probe; however, as rates typically decrease quickly moving away from the probe, the effects of a broad range of rates may be more strongly felt proximate the probe, while the rates in the outer areas of the biological material being treated may be lower (e.g., in the range of 1-10° C./minute) regardless of the rate at which the probe, or other device, is cooled or heated.

One or more probes 18 may be used to cool and/or heat the biological material 12 at a rate effective to destroy at least the portion 14 of the treated biological material. In a further embodiment, for example, when the biological material 12 is cooled with the probe 18, an ice ball is formed. The ice ball formation typically originates proximate the tip of each probe 18. As thermal energy is removed from the tissue, the ice ball grows. Visualizing the size of the ice ball formation may assist in determining the extent, or amount, of tissue and cell material killed during a thermal surgical procedure. Visualization of the size of the ice ball may be accomplished, e.g., through the use of hypaque with fluoroscopy, ultrasonic imaging, MRI, gadolinium with MRI, impedance techniques, or other applicable techniques.

Figure 2:
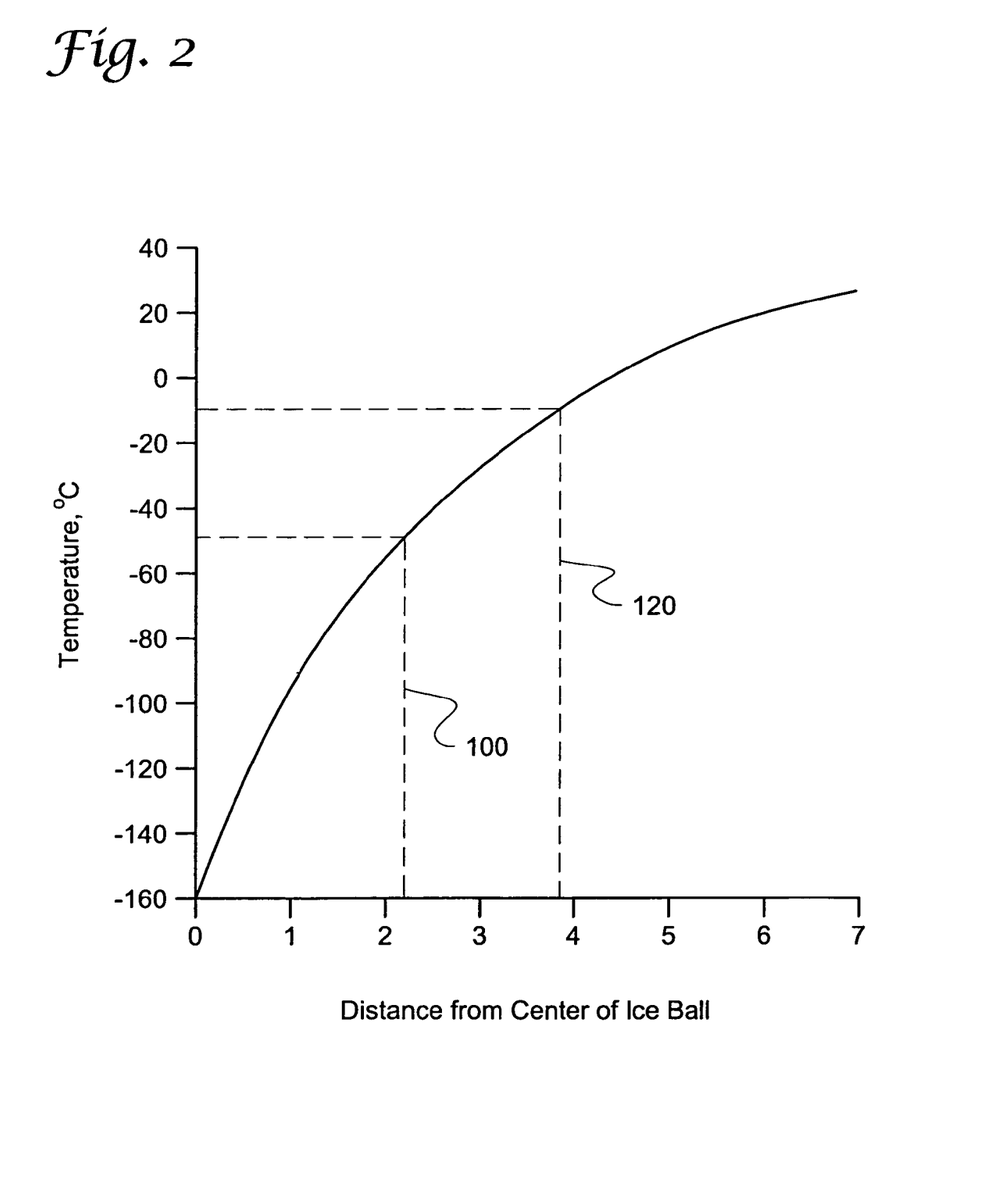
FIG. 2 shows one example of a relationship of temperature versus distance from the center of an ice ball according to the present invention.

FIG. 2 depicts one example of the relationship of temperature versus distance from the ice ball center. Line 100 illustrates the distance from the center of the ice ball (e.g., the location of the probe) where cell death will typically occur for biological material that has not been treated with the inflammation inducing composition. As will be noted, the temperature at the distance where the cell death is suggested to occur within tumors is between approximately −20° C. to approximately −60° C. in the depicted example. In contrast, when the biological material is treated with the inflammation inducing composition the center of the ice ball (e.g., the location of the probe) where cell death will typically occur may be increased along with the temperature at which this cell death occurs. This is illustrated by line 120. Thus, the inflammation inducing composition may effectively increase the distance from the probe, or other device, for which cell death will typically occur without a corresponding increase in the diameter of the ice ball.

In addition to increasing the volume in which cell death will typically occur, the use of the inflammation inducing composition is believed to enable a change in the size or extent of the ice ball such that the use of the composition may, for example, reduce the size of the ice ball. Although not wishing to be bound by any particular theory, it is believed that this may be due, at least in part, to the preconditioned state of the microvasculature of the biological material caused by the introduction of the inflammation inducing composition. A reduction in the size of the ice ball formation coupled with the increase in the volume within which cell death will typically occur in the cryosurgical ice ball results in an ice ball with a size that more closely correlates to the volume in which the actual cell death occurs. Further, the inflammation composition is believed also to enable a change of the temperature at which cell death occurs (the "destruction point") by augmenting the injury zone such that it more closely matches the ice ball or, alternatively, by altering the phase change temperature, thereby potentially decreasing the ice ball size for a given probe operation.

Figure 3:
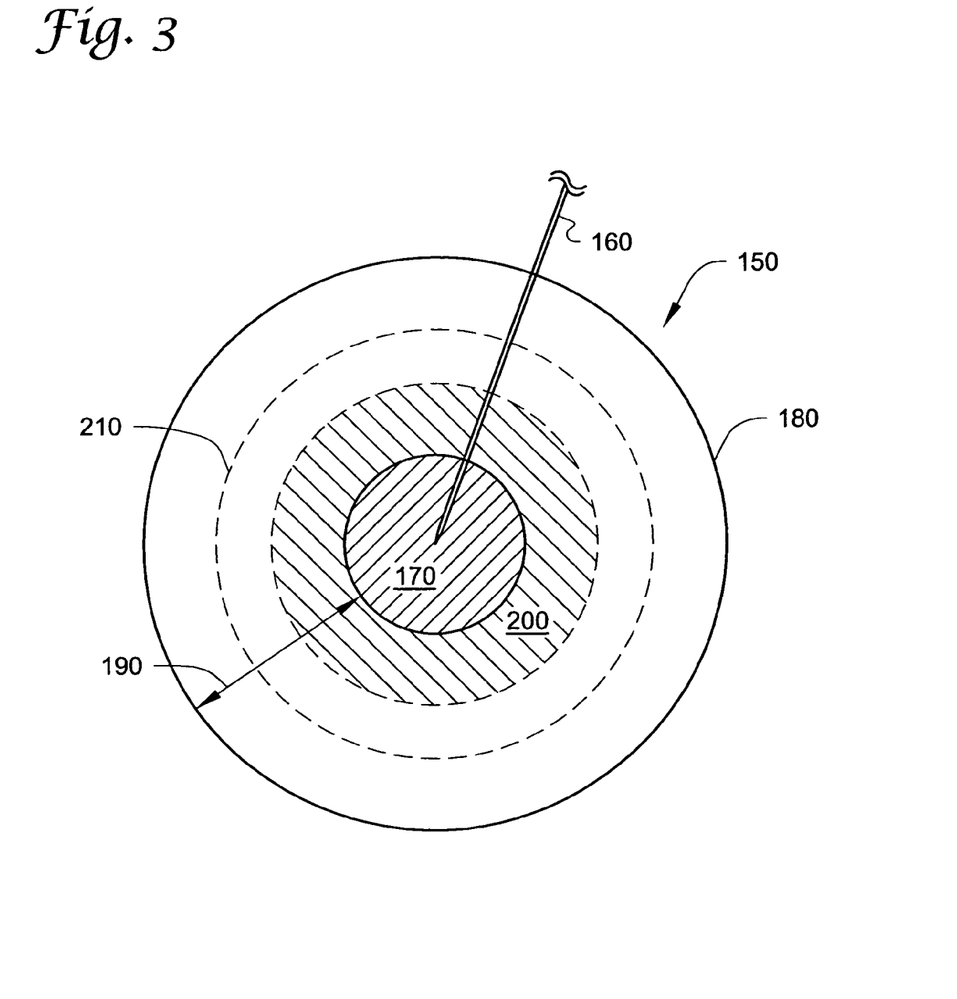
FIG. 3 shows a cross-sectional view of one example of an ice ball according to the present invention.

FIG. 3 illustrates what is believed to occur with respect to the size of an ice ball according to the methods, compositions, and systems of the present invention. The ice ball is shown generally at 150. Probe 160 is used to remove thermal energy from the biological material so as to create the ice ball 150. When the ice ball is formed in biological material not treated with the inflammation inducing composition, a kill zone 170 surrounds the tip of the probe 160, within a boundary 180 of the ice ball 150. As FIG. 3 illustrates the boundary 180 of the ice ball 150 is located at a distance 190 from the edge of the kill zone 170.

In contrast, when the biological material is treated with the inflammation inducing composition according to the present invention, the kill zone 200 may thereby be enlarged as compared to kill zone 170. In addition, the boundary 210 of the ice ball 150 may be reduced as compared to the boundary 180. Thus the size of the ice ball may be reduced and the size of the kill zone within the ice ball may be increased due to administration of the inflammation inducing composition of the present invention. One potential beneficial result of these changes in kill zone and ice ball size is that the kill zone may more closely correlate with the size of the ice ball. This may allow surgeons to more closely predict the actual kill zone created during the thermal surgical procedure and more effectively treat diseased tissues while preserving adjoining normal tissues from injury.

For example, during cryosurgery of the prostate and many other organs such as liver, kidney or brain, ultrasound or MRI can be used to monitor the extent of the cryosurgical ice ball and it is used at some level to predict the outcome of the procedure. The ice ball boundary, however, is typically at a temperature of approximately −0.5° C., while thresholds of prostate cancer destruction are reported anywhere from approximately −20° C. to −60° and in some instances even lower (Hoffmann N, Bischof J. 2002. Urology 60 (Supplement 2A): 40-9; Saliken J, Donnelly B, Rewcastle J C. 2002. Urology (Supplement 2A): 26-33). Thus, while monitoring is useful for imaging the ice ball and predicting likely outcome of the surgery, it may not assist in the outcome that not all of the tissue that is frozen is also effectively treated. In some tissues, such as liver and sometimes kidney, the ice ball may be allowed to progress into a margin of normal tissue beyond the tumor. However, this is not the case with prostate since overfreezing into sensitive adjacent structures such as the rectum and urethra can cause complications such as rectal and urethral fistulas. On the other hand if the surgeon is too conservative and under freezes by keeping the ice ball solely within the prostate, then cancer which often exists under the prostate capsule at the edge of the gland may not be effectively treated leading in some cases to recurrence of disease. One approach of the present invention may include the use of cryosurgical adjuvants in the form of both an inflammation inducing composition and a eutectic freezing point changing agent (such as, e.g., those described in U.S. patent application Ser. No. 10/461,763, entitled CRYOSURGERY COMPOSITIONS AND METHODS, filed Jun. 13, 2003 may be used together. The combination may provide inflammation to the biological material to both increase freeze destruction (salts and TNF-alpha) and reduce the temperature at the edge of the ice ball. The combination may improve the effectiveness and predictability of the kill zone while preserving normal tissues from excessive and/or unnecessary injury.

A composition including the cytokine TNF-alpha was used to increase the threshold temperature of destruction after cryosurgery in human prostate cancer (LNCaP grown in nude mice) to a mean temperature above 0° C. The local use of TNF-alpha to pre-inflame prostate cancer increased the ability of freezing to destroy the cancer. Thus, monitoring techniques such as ultrasound, CT, MR, and others which focus on the edge of the ice ball may, in the presence of TNF-alpha, also be capable of predicting the outcome of the treatment by measuring the edge of the injury at the same time that the edge of the ice ball is measured.

Pre-inflammation of biological tissue may be a mechanism useful in accentuating vascular injury during thermal surgical procedures. In addition, there may be a role for the endothelium in shutting down the microvascular supply to prostate cancers (Dunning AT-1) grown in Copenhagen rats fitted with dorsal skin fold chambers (DSFC) (Hoffmann N, Bischof J. 2002. Urology 60 (Supplement 2A): 40-9). Data from these studies indicates that the tumor could under some freeze/thaw conditions survive freezing to −80° C. and below in vitro, but that moderate freezing and thawing to about −20° C. leads to vascular stasis and histological necrosis by ischemia as assessed at day 3 after the freeze in both the cancer and normal rat skin in vivo.

The accentuation of the vascular mechanism of injury has been approached by focusing on inflammation. The role of the endothelium suggested the possibility of creating a pre-existing non-destructive inflammation within the tissue prior to the freeze. The cytokine TNF-alpha is known to upregulate NF-kB and various adhesion molecules within endothelium and has also recently been used in the DSFC (Fukumura D et al. 1995. Cancer Research 55: 4824-9). As discussed herein, local TNF-alpha delivery is an effective way to achieve pre-inflammation prior to a thermal surgical procedure.

EXAMPLES

The following are examples are provided to illustrate the present invention and are not intended to limit the present invention thereto in any manner

Example 1

The dorsal skin flap chamber (DSFC) of male athymic nude mice was seeded with the tumor LNCaP Pro 5 human prostate cancer, inflamed with TNF-alpha, subjected to cryosurgery, and assessed according to the following procedure.

The dorsal skin of a male athymic nude mouse was sandwiched between two identical anodized aluminum frames, a 19 millimeter (mm) by 22 mm chamber was mounted onto the mouse by three screws, the skin was attached to the chamber with 4-O silk using suture holes, and the skin on the side of the viewing region was removed, exposing the dermis containing the microvasculature on the opposite side of the skin.

To provide chambers having tumors, approximately $5 \times 10^6$ LNCaP Pro 5 human prostate tumor cells were mixed with MATRIGEL matrix (BD Biosciences, Bedford, Mass.) as described by Lim et al. (Prostate, 22:109-118 (1993)). Approximately 30 µl of the cell suspension was applied to the surface of the microvascular bed immediately after the initial chamber implantation and the tumor was allowed to grow for 10 days, the skin reaching a total thickness of about 450 micrometers (µm) and the tumor extending approximately 10 mm in diameter.

A local application of 20 µl of a 10 ng/ml TNF-alpha (total application of 0.2 ng) was applied to the tumor tissue within the DSFC for about 15 minutes, after which the TNF-alpha solution was wicked off and the tissue was covered with a glass window. After four (4) hours, the mouse was anesthetized, TNF-alpha-induced inflammation was measured by observation of leukocyte rolling, and thereafter cryosurgery was immediately performed in the inflamed tissue.

The cryosurgery was performed with an argon-cooled, 5 mm diameter cryoprobe (EndoCare, Irvine, Calif.) activated for a cooling time of 5 minutes and a target temperature of −160° C., which corresponded to an average external probe end temperature of about −125° C. Type "T" thermocouples (Omega Tech. Corp, Stamford, Conn.), having a 0.5 mm bead diameter, were inserted into the tissue and were used to measure the average external probe end temperature. The temperature at each thermocouple was recorded using a HYDRA DATA LOGGER SERIES 2 (Fluke, Everett, Wash.).

After the cryosurgery the probe was turned off and the tissue was allowed to thaw passively at room temperature.

The vasculature was imaged using a 70 kD fluorescein isothiocyanate (FITC)-labeled dextran (Molecular Probes, Eugene Oreg.). At 3 days post-treatment, 0.05 ml of a solution of FITC-labeled dextran (10 mg dextran/ml PBS (Gibco BRL, Gaithersburg, Md.)) was injected into the tail vein of the mouse. The dorsal skin flap chamber was then illuminated with a mercury lamp and a FITC signal-enhancing filter ($\lambda$=470-490 nm) to view the contrast fluorescence. A Silicon Intensified Transmission camera (Hamamatsu, North Central Instruments, Twin Cities, Minn.) was used to detect the fluorescent signal, and the signal was recorded with a JVC S-VHS video recorder (JVC Company of America, Aurora, Ill.).

Hstological analysis of the entire tissue was performed at day 3 post-cryosurgery according to Hoffmann et al. (ASME J. Biomechanical Engineering 123:310-316 (2001)), and images of the histology were taken on an Olympus BX-50 upright microscope (Leeds Precision Instruments, Minneapolis, Minn.). The end temperature of the cryolesion and the thermal parameters within the cryosurgical ice ball were calculated according to the methods of Chao et al. (Cryobiology, 2004 (in press)).

The above example was repeated a total of 9 times to provide data for TNF-alpha-treated tumor tissue, and was repeated a total of 13 times without TNF-alpha treatment.

Results:

The area of vascular injury was observed with FITC-labeled dextran. The results showed a substantially complete destruction of the vasculature in the center of the lesion and an abrupt change to normal patency moving radially outward. It was determined that regions of vascular stasis lead directly to tissue necrosis. Further, the edge of the static zone (i.e., the zone of vascular stasis) at day 3 post cryosurgery in tissues inflamed with TNF-alpha was at a radius greater than that for tissues that were not inflamed with TNF-alpha ($r$=3.81±0.29 mm in LNCaP Pro 5 tumor tissues without TNF-alpha treatment and $r$=4.07±0.34 mm in tissues with TNF-alpha treatment). Additionally, the edge of the static zone extended beyond the edge of the ice ball for LNCaP Pro 5 tumor tissues that were treated with TNF-alpha, whereas the edge of the static zone stayed within the edge of the ice ball in inflamed normal skin tissues that were treated with TNF-alpha (Example 2, below).

The minimum temperature required for causing necrosis was 3.5±6.9° C. in TNF-alpha-treated LNCaP Pro 5 tumor tissue. Compared to tissues without TNF-alpha treatment, where the minimum temperature required for causing necrosis was −16.5±4.3° C. in LNCaP Pro 5 tumor tissue, the results indicate that the local use of TNF-alpha can increase the threshold temperature of cryo-destruction by more than 10° C.

Example 2

The procedure according to Example 1 was repeated, with the exception that the biological material treated was normal nude mouse hypodermis (i.e., normal skin).

Example 2 was repeated a total of 9 times to provide data for TNF-alpha-treated normal tissue, and was repeated a total of 14 times without TNF-alpha treatment.

Results:

Similar, results were obtained in normal nude mouse hypodermis without tumors. Inflammation induced by TNF-alpha moved the edge of the static zone closer to the edge of the cryosurgical ice ball ($r$=3.99±0.13 mm in tissues treated with TNF-alpha, as compared with $r$=3.13±0.39 mm in tissues without TNF-alpha treatment), and the minimum temperature required for cryo-destruction was −9.8±5.8° C. in TNF-alpha-treated normal skin as compared with −24.4±7.0° C. in untreated normal skin.

Cell suspensions of human endothelial cells (MVECs) were used to assess the enhancement of direct cellular injury (DCI) by use of an adjuvant, wherein the adjuvant used is TNF-alpha.

Example 3

Measuring Enhancement of DCI in MVEC Endothelial, MCF-7 Breast Cancer and LNCaP Pro 5 Prostate Cancer Cells by TNF-alpha Addition Human dermal microvascular endothelial cells (MVEC) were prepared and grown as adherent monolayers as described by Gupta et al., Experimental Cell Research, 230:244-251 (1997), maintained in a 37° C./5% $CO_2$/95% humidified air environment in T-flasks pre-coated with 1% gelatin in MCDB 131 medium supplemented with 20% heat-inactivated human male serum, hydrocortisone, cAMP, L-glutamine, heparin, endothelial cell growth supplement (Vec Tec, Schenectady, N.Y.) and antibiotics. LNCaP cells were cultured as adherent monolayers in DMEM/F12 medium supplemented with 10% FBS, antibiotics and dihydrotesterone (DHT). MCF-7 cells were grown in similar medium with the following exception: 5% (rather than 10%) FBS, antibiotics and insulin (no DHT). Cells were subcultured by rinsing with Hank's balanced salt solution (HBSS), followed by light trypsinization, enzyme neutralization, and reseeding.

One to three days prior to TNF-alpha exposure and/or freezing, cells were reseeded onto 96-well plates for apoptosis/necrosis assay and onto T-flasks for EMSA or Western blots, as monolayers or in Petri dishes as collagen gels (live-dead assay). Each sample was then exposed to medium with TNF-alpha at concentrations from 10 nanogram per milliliter (ng/ml) to 1 microgram per milliliter (µg/ml) for 4 to 48 hours.

Control and experimental F/T groups were then assessed for cell viability at varying time points starting 3 hours after intervention. Cell viability was measured microscopically by a fluorescent dye assay (cell viability assay) by an apoptotic/necrotic assay.

The fluorescent dye assay was used to assess the plasma membrane integrity of cells immediately before (control) and after F/T using Hoechst 33342 and propidium iodide (PI). Each dye has affinity to nucleic acid, i.e. all cells regardless of viability take up Hoechst and only plasma membrane compromised cells take up PI. Cells were incubated with 9 µM Hoechst 33342 and 7 µM PI for 15 minutes at 37° C., placed on a microslide, cover-slipped and the percentage of dead cells/field determined at 200× using a fluorescent microscope (Olympus BX-50, Tokyo, Japan).

The apoptosis/necrosis assay was used to map thermal/adjuvant conditions that triggered apoptosis. The cells were stained with fluorescent Annexin V.

The fluorescent dye assay was performed with at least 5 representative fields and a total of 100-200 cells/sample were counted. All samples were measured in four or six replicates and the resulting values were averaged.

Results:

TNF-alpha was shown to increase cryosensitivity of the MVEC, MCF-7 and LNCaP Pro 5 cells in vitro. The action of the TNF-alpha predominantly inflamed cells, and the inflamed cells exhibited increased necrosis in vitro.

All references identified herein are incorporated by reference in their entirety as if each were incorporated separately. This invention has been described with reference to illustrative embodiments and is not meant to be construed in a limiting sense. Various modifications of the illustrative embodiments, as well as additional embodiments of the invention, will be apparent to persons skilled in the art upon reference to this description.

What is claimed is:

1. A method of performing a thermal surgical procedure, comprising:
    identifying biological material to undergo the thermal surgical procedure; contacting the biological material with an inflammation inducing composition, wherein inflammation is induced in at least a portion of the identified biological material; and
    adjusting the temperature of the identified biological material, wherein at least a portion of the biological material is destroyed after undergoing the thermal surgical procedure;
    wherein the biological material is contacted with the inflammation inducing composition from about 1 hour to about 4 hours prior to adjusting the temperature of the biological material.

2. The method of claim 1 wherein adjusting the temperature comprises lowering the temperature below a physiological temperature of the biological material.

3. The method of claim 1 wherein adjusting the temperature comprises raising the temperature above a physiological temperature of the biological material.

4. The method of claim 1 wherein the biological material is selected from the group consisting of cells, tissues, and combinations thereof.

5. The method of claim 4 wherein the cells are tumor cells.

6. The method of claim 4 wherein the tissues are selected from the group consisting of tumor tissues, liver tissue, prostate tissue, breast tissue, kidney tissue, vascular tissue, gastrointestinal tissue, muscle tissue, skin tissue, connective tissues, and combinations thereof.

7. The method of claim 1 wherein the inflammation inducing composition comprises one component selected from the group consisting of at least one virus, at least one bacterium, ethanol, cytokines, interleukins, chemokines, oxygen-free radicals, bacterial lipopolysaccharides, and combinations thereof.

8. The method of claim 7 wherein the cytokine is selected from the group consisting of TNF-alpha, truncated versions of TNF-alpha, and combinations thereof.

9. The method of claim 1 wherein the inflammation inducing composition comprises a carrier selected from the group consisting of a saline solution, encapsulation in microbeads, encapsulation in nanobeads, retroviral gene therapy, impregnated gelfoam, and combinations thereof.

10. A method of performing a thermal surgical procedure, comprising:
    identifying biological material to undergo the thermal surgical procedure;
    contacting the biological material with an inflammation inducing composition for an interval of about 4 hours to about 48 hours, wherein inflammation is induced in at least a portion of the identified biological material; and
    after the interval adjusting the temperature of the identified biological material, wherein at least a portion of the biological material is destroyed after undergoing the thermal surgical procedure.

11. The method of claim 10 wherein adjusting the temperature comprises lowering the temperature below a physiological temperature of the biological material.

12. The method of claim 10 wherein adjusting the temperature comprises raising the temperature above a physiological temperature of the biological material.

13. The method of claim 10 wherein the biological material is selected from the group consisting of cells, tissues, and combinations thereof.

14. The method of claim 13 wherein the cells are tumor cells.

15. The method of claim 13 wherein the tissues are selected from the group consisting of tumor tissues, liver tissue, prostate tissue, breast tissue, kidney tissue, vascular tissue, gastrointestinal tissue, muscle tissue, skin tissue, connective tissues, and combinations thereof.

16. The method of claim 10 wherein the inflammation inducing composition comprises one component selected from the group consisting of at least one virus, at least one bacterium, ethanol, cytokines, interleukins, chemokines, oxygen-free radicals, bacterial lipopolysaccharides, and combinations thereof.

17. The method of claim 16 wherein the cytokine is selected from the group consisting of TNF-alpha, truncated versions of TNF-alpha, and combinations thereof.

18. The method of claim 10 wherein the inflammation inducing composition comprises a carrier selected from the group consisting of a saline solution, encapsulation in microbeads, encapsulation in nanobeads, retroviral gene therapy, impregnated gelfoam, and combinations thereof.

* * * * *